United States Patent
Hovey et al.

(10) Patent No.: US 7,281,699 B2
(45) Date of Patent: Oct. 16, 2007

(54) UNIVERSAL ACCOMMODATING IOL HOLDER FOR LENS PROCESSING AND PACKAGING

(75) Inventors: Larry C. Hovey, Ontario, NY (US); Charles P. Henning, Rochester, NY (US); Wen X. Jin, Victor, NY (US); Ted Foos, Rochester, NY (US); William J. Appleton, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 264 days.

(21) Appl. No.: 10/747,393

(22) Filed: Dec. 29, 2003

(65) Prior Publication Data

US 2005/0143813 A1 Jun. 30, 2005

(51) Int. Cl.
*B29D 11/00* (2006.01)
(52) U.S. Cl. .................. 249/205; 206/5.1; 206/438; 425/808
(58) Field of Classification Search ............... 249/205; 425/808; 206/5.1, 438
See application file for complete search history.

(56) References Cited

U.S. PATENT DOCUMENTS

| 4,104,339 | A | 8/1978 | Fetz et al. |
| 4,173,281 | A | 11/1979 | Trought |
| 4,205,747 | A | 6/1980 | Gilliam et al. |
| 4,257,521 | A | 3/1981 | Poler |
| 4,269,307 | A | 5/1981 | LaHaye |
| 4,402,396 | A | 9/1983 | Graham |
| 4,423,809 | A | 1/1984 | Mazzocco |
| 4,508,216 | A | 4/1985 | Kelman |
| 4,615,703 | A | 10/1986 | Callahan et al. |
| 4,684,014 | A | 8/1987 | Davenport |
| 4,697,697 | A | 10/1987 | Graham et al. |
| 4,736,836 | A * | 4/1988 | Alongi et al. ................ 206/5.1 |
| 4,817,789 | A | 4/1989 | Paul |
| 4,844,242 | A | 7/1989 | Chen et al. |
| 4,897,981 | A | 2/1990 | Beck |
| 4,928,815 | A | 5/1990 | Paul |
| 5,176,686 | A | 1/1993 | Poley |

(Continued)

FOREIGN PATENT DOCUMENTS

JP     2001346817     12/2001

(Continued)

OTHER PUBLICATIONS

Jin, et al., "Lens Mounting Fixture for Accommodating IOL," U.S. Appl. No. 10/747,609, filed Dec. 29, 2003.

(Continued)

*Primary Examiner*—Tim Heitbrink
(74) *Attorney, Agent, or Firm*—Jeffrey B. Powers

(57) ABSTRACT

The present invention provides a holder for supporting a two optic accommodating intraocular lens device. The holder is capable of holding the device while taking measurements or performing manufacturing process steps on the device and/or packaging the device. In a preferred embodiment, the holder supports the device along the haptics thereof such that the optics remain untouched and unobstructed by the holder. As such, testing and/or processing of the optics during their accommodative and unaccomodative positions may be taken, and the device may be safely packaged and shipped with the holder.

10 Claims, 3 Drawing Sheets

U.S. PATENT DOCUMENTS

| | | |
|---|---|---|
| 5,257,521 A | 11/1993 | Castricum |
| 5,275,623 A | 1/1994 | Sarfarazi |
| 5,281,227 A | 1/1994 | Sussman |
| 5,556,400 A | 9/1996 | Tunis |
| 5,589,024 A | 12/1996 | Blake |
| 5,674,284 A | 10/1997 | Chang et al. |
| 6,183,513 B1 * | 2/2001 | Guenthner et al. ........ 623/6.12 |
| 6,360,883 B1 | 3/2002 | Haq et al. |
| 6,386,357 B1 | 5/2002 | Egawa |
| 6,423,094 B1 | 7/2002 | Sarfarazi |
| 6,488,708 B2 | 12/2002 | Sarfarazi |
| 6,797,004 B1 | 9/2004 | Brady et al. |
| 2003/0078658 A1 | 4/2003 | Zadno-Azizi |
| 2003/0209452 A1 | 11/2003 | Mitomo et al. |
| 2003/0214139 A1 | 11/2003 | Nigam |
| 2004/0238980 A1 * | 12/2004 | Kyburz et al. ............... 264/2.5 |

FOREIGN PATENT DOCUMENTS

| | | |
|---|---|---|
| JP | 2002/102261 | 4/2002 |
| WO | WO 00/61036 A1 | 10/2000 |
| WO | WO 02/071983 A1 | 9/2002 |
| WO | WO 02/098327 A1 | 12/2002 |
| WO | WO 03/045285 A1 | 6/2003 |
| WO | WO 2005/065590 A1 | 7/2005 |
| WO | WO 02/096322 A1 | 12/2005 |

OTHER PUBLICATIONS

Jin et al., "Holder for Dual-Optic IOL," U.S. Appl. No. 10/920,623, filed Aug. 18, 2004, pending.

* cited by examiner

UNIVERSAL ACCOMMODATING IOL HOLDER FOR LENS PROCESSING AND PACKAGING

BACKGROUND OF THE INVENTION

The present invention relates to optical lens holders used for performing tests or other processes on the lens and/or packaging the lens. More particularly, the present invention relates to a holder for supporting an accommodating intraocular lens device having at least two optics interconnected by one or more haptics.

Intraocular lenses having a single optic have been known and used for many years. More recently, accommodating intraocular lens devices having two optics interconnected by one or more haptics have been disclosed in the following U.S. patents and applications to Faezeh Sarfarazi, the entirety of which are incorporated herein by reference:

U.S. Pat. No. 5,275,623 "Elliptical Accommodative Intraocular Lens For Small Incision Surgery";

U.S. Pat. No. 6,423,094 "Accommodative Lens Formed From Sheet Material";

U.S. Pat. No. 6,488,708 "Open Chamber Elliptical Accommodative Intraocular Lens System";

U.S. Ser. No. 10,445,762 filed on May 27, 2003 entitled "Mold for Intraocular Lens".

The Sarfarazi accommodating lens device includes two optics, one negative and the other positive for placing in the evacuated lens capsule of an eye. The optics are interconnected along their peripheries by one or more haptics which space the optics from each other and assist in properly positioning the device in the eye. The haptics are formed from a flexible material such that they may flex in response to forces exerted by the eye's ciliary muscles which control accommodation. The haptics will thus flex and bow further radially outwardly upon a compressive force being applied to the device, whereby the two optics are drawn closer together to achieve an accommodative effect in the eye. When the ciliary muscles relax, the haptics flex in the opposite direction (toward a straightened position) causing the optics to space further apart and the lens device returns the eye to its natural, unaccommodative state.

As stated above, single optic intraocular lenses have been known and used for decades while the two lens accommodative intraocular lens device is new and not yet seen on the market. It will be appreciated that manufacturing a two optic lens device presents issues not present in the manufacture of single optic intraocular lenses. During design and manufacture of intraocular lenses, certain measurements must be taken of the device to ensure the device achieves its design parameters. Such measurements require not only that the device be held stationary, but also not interfere with the optic pathway. Furthermore, in a two optic device, the optics must be able to be moved in a manner simulating their accommodative movements in the eye. The holder for such a device must therefore be able to hold the device stationary while also allowing relative movement of the optics. Besides the taking of measurements, manufacturing process steps may need to be carried out such as polishing, for example. The holder should therefore also be able to support the device during manufacturing process steps without damage to the device. It would furthermore be desirable to have a holder for safely packaging and shipping the device to a user.

SUMMARY OF THE INVENTION

The present invention provides a holder for supporting a two optic accommodating intraocular lens device. The holder is capable of holding the device while taking measurements or performing manufacturing process steps on the device. The holder may also be used for packaging and shipping the device. In a preferred embodiment, the holder supports the device along the haptics thereof such that the optics remain untouched and unobstructed by the holder. As such, testing and/or processing of the optics during their accommodative and unaccomodative positions may be taken.

The holder includes a base having at least one but preferably three haptic fingers attached to the base, whereby the intraocular lens device may be removably attached to the holder by supporting the haptics thereof on the haptic fingers of the base, respectively. The haptic fingers may be attached to the base by a respective post with the fingers lying spaced above and parallel to the base. A haptic stop having at least one but preferably three stop posts may be provided for selectively aligning with the haptic fingers to capture the haptics, respectively, when the intraocular lens device is attached to the holder. The stop posts may be attached to a ring having a groove for engaging a rib formed about the perimeter of the base whereby the haptic stop may be rotationally coupled to the base. The haptic stop is movable between engaged and unengaged positions with respect to the haptic fingers, respectively, thereby allowing the intraocular lens device to be alternately mounted and dismounted from the holder. When the intraocular lens device is supported on the holder, the optics thereof lie spaced above and parallel to the base whereby they may be moved relative to each other when performing tests thereon.

DETAILED DESCRIPTION

Figure 1A:
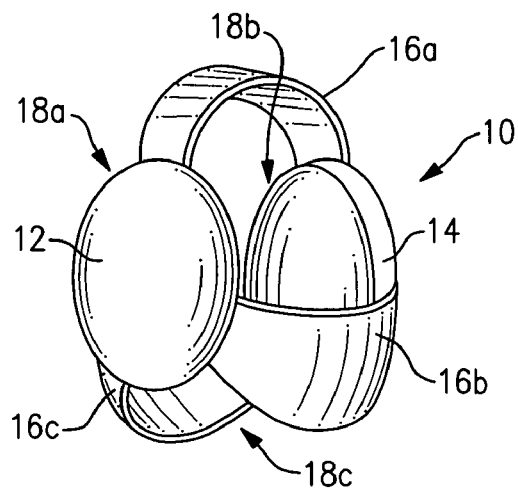
FIG. 1A is a perspective view of an embodiment of an accommodative intraocular lens which may be supported by the holder of the present invention.
Figure 1B:
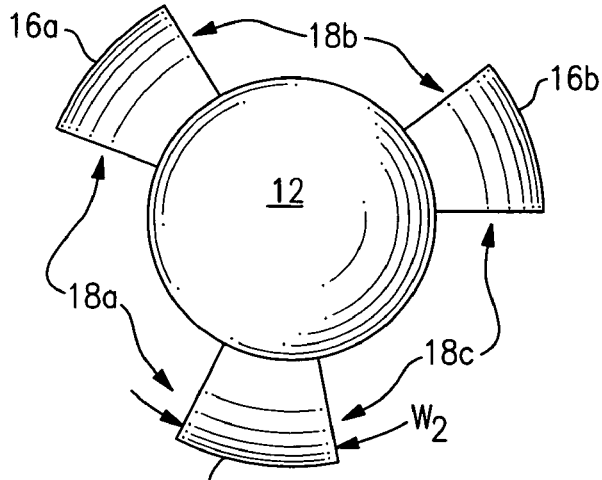
FIG. 1B is a plan view thereof.
Figure 1C:
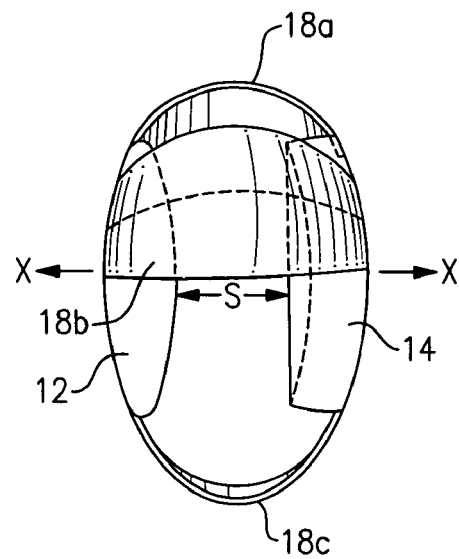
FIG. 1C is a side elevational view thereof.

Referring now to the drawing, there is seen in FIGS. 1A-C a representative embodiment of an accommodative intraocular device 10 which may be supported by the present invention. Briefly, lens device 10 includes first and second optics 12, 14 interconnected by one or more, but preferably three haptics 16a, 16b and 16c defining three open spaces 18a, 18b, 18c therebetween, respectively. Haptics 16a-c bow outwardly past the optic perimeters 12p, 14p and are flexible whereby the optics may move alternately toward and away from each other generally along the optical axis x-x. FIGS. 1A and 1C show the space "S" between the optics 12, 14 which gets smaller as the optics move toward one another and larger as the optics move away from one another. It is understood that the present invention is a holder for a lens device and therefore the particular optic and haptic configurations of a lens device which may be supported by the inventive holder may vary from that shown and described herein.

Figure 2A:
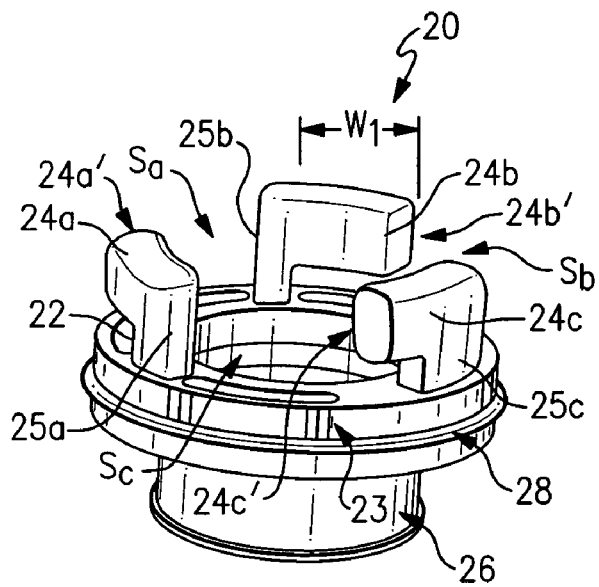
FIG. 2A is a perspective view of an embodiment of the base component of the inventive holder.
Figure 2B:
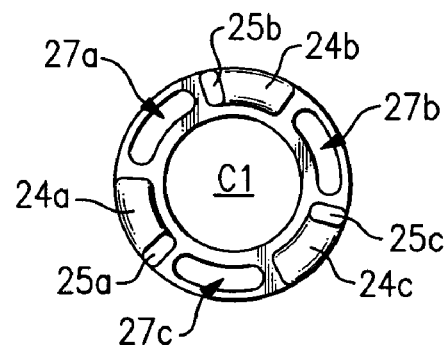
FIG. 2B is a top plan view of FIG. 2A.

Turning to FIG. 2, the base component of the holder is indicated generally by reference numeral 20. Base component 20 includes a support surface 22 having three annularly spaced haptic fingers 24a, 24b and 24c. In the preferred embodiment, support surface 22 is in the shape of a ring having an open, circular center $C_1$ (see FIG. 2B). The haptic fingers 24a-c thus define three spaces Sa, Sb and Sc therebetween and are used to support the lens device haptics 16a-c, respectively. In this regard, it is noted that the number of haptic fingers should correspond to the number of haptics on the particular device 10 being supported thereby. For example, in a lens device having two haptics, only two haptic fingers are required on base 20; in a lens device having four haptics, four haptic fingers are required, etc.

The haptic fingers 24a-c each are preferably supported by a post 25a-c which extend substantially perpendicularly up from support surface 22. The width $W_1$ of the haptic fingers (FIG. 2) should by slightly smaller than the corresponding width $W_2$ of the haptic (FIG. 1B) on which it is supported to prevent side-to-side slippage of the haptic on the support finger during testing or processing of the lens device thereon. This will be described in more detail below.

Base 20 may further include means for removably mounting base 20 to a work surface or fixture, e.g., an optical bench (not shown). One such means may take the form of a cylindrical sleeve 26 which may be fit over a corresponding cylinder of the work surface not shown). It is understood that the mounting means may take a variety of configurations and the invention is not to be limited to the exact configuration and placement of sleeve 26 shown and described herein. It will be appreciated that by making the holder removably mountable to a work surface or other fixtures, the holder may be conveniently moved from one work surface or fixture to another when performing different tests or processes on the lens device 10.

Figure 3:
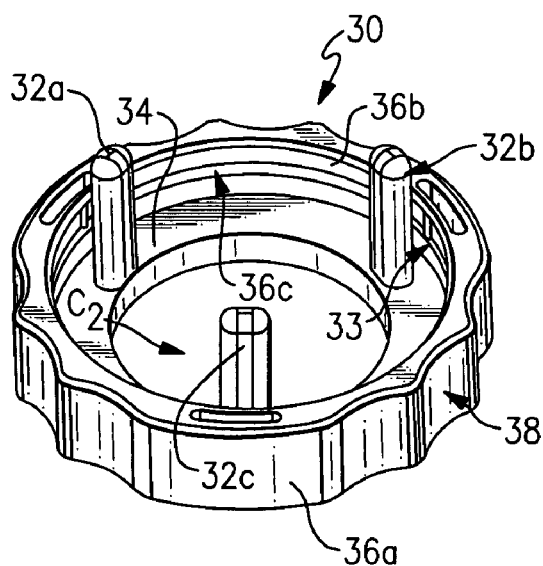
FIG. 3 is a perspective view of the haptic stop component of the inventive holder.
Figure 4:
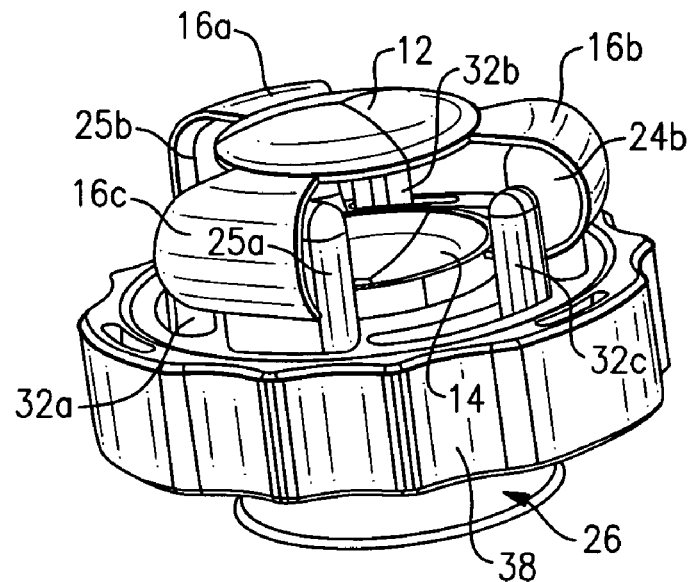
FIG. 4 is a perspective view of the base and haptic stop components coupled together and supporting the intraocular lens device of FIGS. 1A-C in the intended manner.
Figure 5:
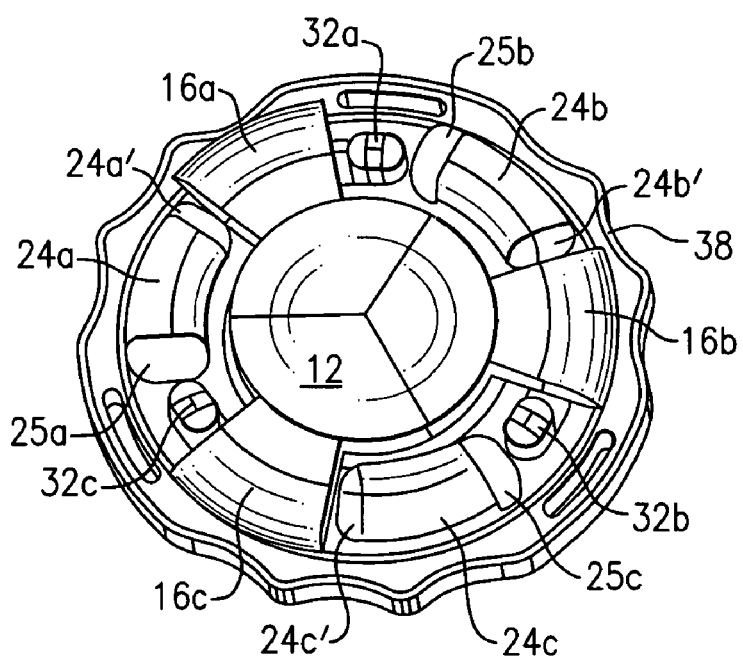
FIG. 5 is a top plan view of FIG. 4 except the haptic stop component has been rotated to its unengaged position relative to the haptic fingers of the base component.

Referring to FIG. 3, the haptic stop component of the device is indicated generally by the reference numeral 30. Haptic stop 30 includes three stop posts 32a, 32b and 32c for aligning with haptic fingers 24a, 24b and 24c, respectively, in the manner to be described. The number of stop posts should equal the number of haptic fingers. The stop posts 32a-c may be mounted to a support surface 34 and extend substantially perpendicularly therefrom. Support surface 34 may be surrounded by a ring 36 having an exterior surface 36a and interior surface 36b. In the preferred embodiment, interior surface 36b includes an annular groove 36c for engaging with an annular rib 28 provided on the exterior surface of base support surface 22. The fit between groove 36c and rib 28 should removably couple the components together yet also permit the components to be freely rotated with respect to one another wherein rib 28 "rides" in groove 36c. To initially couple the base 20 to the haptic stop 30, the stop posts 32a-c of haptic stop 30 are extended up through annular slots 27a, 27b and 27c formed in support surface 22 of base 20 between haptic fingers 24a, 24b and 24c, respectively (FIGS. 2B, 4 and 5). The haptic stop 30 is pressed upwardly against base 20 until rib 28 snap fits into groove 36c. In the preferred embodiment, haptic stop support surface 34 is ring shaped and includes an open, circular center $C_2$. The outer surface of support surface 34 is preferably provided with a plurality of finger indentations 38 to permit easy manual rotation of haptic stop 34 with respect to base 20.

FIG. 5 shows a top plan view of the inventive holder with base 20 and haptic stop 30 in the coupled, unlocked position and the lens device haptics 16a-c located in spaces Sa-c. In the initial, unlocked position, stop posts 32a, 32b, 32c lie adjacent posts 25b, 25c, 25a, respectively. In this position, clearance is provided between the stop post and the haptic finger free ends 24a'-c' wherethrough the haptics of the lens device may pass. It is noted that the spaces defined between the stop post and adjacent haptic finger free end is wide enough to accommodate the haptics 16a-c therein respectively, which thereby allows the lens device to be alternately mounted and removed from the holder (seen best in FIG. 5).

The lens device 10 may then be carefully rotated to position the haptics 16a-c thereof over the haptic fingers 25a-c of the base component 20, respectively. This may be done manually using a pair of tweezers, for example, with care not to damage the lens device. Once the haptics have been positioned over their respective haptic fingers, the haptic stop 30 may be rotated with respect to the base 20 whereby the stop posts 32a-c are moved to the opposite end of their respective slots 27a-c, coming to rest adjacent the free end 24a'-c' of a respective haptic finger 24a-c. The haptic 16a-c is thus "captured" on its respective haptic finger 24a-c by the stop post 32a-c at one end and the haptic finger post 25a-c on the other end. This "locked" position is depicted in FIG. 4. One or more sets of cooperative locating bosses and notches 23 (FIG. 2) and 33 (FIG. 3) may be formed on the facing surfaces of the base and haptic stop, respectively, to further secure the base and haptic stop components in the locked position.

Since the component central circular openings $C_1$, and $C_2$ are concentric when in the coupled condition, the lens device optics 12 and 14 are unobstructed by the holder and may be tested and/or processed as desired. Furthermore, the optics may be forced closer together or farther apart while supported on the holder to perform accommodation tests on the lens device as desired. Once testing and/or processing is complete, the lens device 10 may be removed from the holder by rotating the haptic stop 30 relative to the base component 20 in the opposite direction to the "unlocked" position seen in FIG. 5. The lens device haptics 16a-c are then carefully moved off of their respective haptic fingers 24a-c and the lens device 10 is lifted away from the holder.

What is claimed is:

1. A holder for an intraocular lens device having first and second optics interconnected by at least two haptics, said holder comprising:
   a) a base having an opening;
   b) at least two posts extending from said base, the posts being disposed about said opening;
   c) at least two haptic fingers, each haptic finger attached to a respective one of said posts, said fingers lying spaced above said base, each of the at least two haptic fingers extending from its corresponding post in a same rotational direction about the opening; whereby said intraocular lens device may be removably attached to said holder by relative rotational movement of the haptics and the fingers, such that haptics are moved onto the haptics fingers and such that the at least two haptics are supported by the at least two haptic fingers.

2. The holder of claim 1 whereby said holder supports said intraocular lens device with said first and second optics lying in spaced relation to each other.

3. The holder of claim 1 and further comprising a haptic stop having at least two stop posts for selectively aligning with said at least two haptic fingers to capture said at least two haptics, respectively, when said intraocular lens device is attached to said holder.

4. The holder of claim 1 and further comprising a shaft extending from said base for mounting said base to a fixture.

5. The holder of claim 3 whereby said base and said haptic stop may be removably coupled.

6. The holder of claim 5 wherein said base and said haptic stop may he coupled by a mating rib and groove formed thereon, respectively.

7. A holder for an intraocular lens device having first and second optics interconnected by at least three haptics, said holder comprising:
   a) a base having an opening;
   b) at least three posts extending from said base, the posts being disposed about said opening;
   c) at least three haptic fingers, each haptic finger attached to a respective one of said posts, said fingers lying spaced above said base;
   whereby said intraocular lens device may be removably attached to said holder by supporting the at least three haptics on the at least three haptic fingers.

8. The holder of claim 7 wherein the posts are disposed substantially annularly about said opening.

9. The holder of claim 1, wherein each of the at least two fingers extends from its corresponding post in a direction parallel to the base.

10. The holder of claim 7, wherein each of the at least three fingers extends from its corresponding post in a direction parallel to the base.

* * * * *